United States Patent [19]
Goldmann

[11] Patent Number: 5,722,992
[45] Date of Patent: Mar. 3, 1998

[54] IMPLANT, ITS USE IN SURGERY AND PROCESSES FOR THE PRODUCTION THEREOF

[75] Inventor: Helmut Goldmann, Melsungen, Germany

[73] Assignee: B. Braun Surgical GmbH, Melsungen, Germany

[21] Appl. No.: 663,478

[22] Filed: Jun. 13, 1996

[30] Foreign Application Priority Data

Jun. 14, 1995 [DE] Germany .................. 195 21 642.3

[51] Int. Cl.⁶ .................................................. A61B 17/00
[52] U.S. Cl. ........................ 606/228; 606/151; 623/13
[58] Field of Search ........................ 606/151, 154, 606/76, 77, 69, 228, 229, 230, 231, 232; 623/13, 16; 602/904, 43

[56] References Cited

U.S. PATENT DOCUMENTS

| | | | |
|---|---|---|---|
| 4,442,133 | 4/1984 | Greco et al. | 427/2 |
| 4,563,485 | 1/1986 | Fox, Jr. et al. | 523/113 |
| 4,581,028 | 4/1986 | Fox, Jr et al. | 623/2 |
| 4,612,337 | 9/1986 | Fox, Jr. et al. | 523/113 |
| 4,740,382 | 4/1988 | Greco et al. | 427/2 |
| 4,749,585 | 6/1988 | Greco et al. | 427/2 |
| 5,197,977 | 3/1993 | Hoffman, Jr. et al. | |
| 5,268,178 | 12/1993 | Calhoun et al. | 424/426 |
| 5,540,773 | 7/1996 | Chesterfield et al. | 118/67 |
| 5,578,046 | 11/1996 | Liu et al. | 606/151 |
| 5,607,474 | 3/1997 | Athanasiou et al. | 623/11 |

FOREIGN PATENT DOCUMENTS

| | | |
|---|---|---|
| 0087662 | 9/1983 | European Pat. Off. |
| 0 207 624 | 5/1985 | European Pat. Off. |
| 0173186 | 5/1986 | European Pat. Off. |
| 0 328 421 | 4/1993 | European Pat. Off. |
| 3503126 | 1/1985 | Germany |
| 3913926 | 10/1990 | Germany |
| 2153235 | 8/1985 | United Kingdom |

*Primary Examiner*—Jeffrey A. Schmidt
*Attorney, Agent, or Firm*—Pennie & Edmonds

[57] ABSTRACT

An implant at least partly comprises and at least on the infection-protected surface areas of resorbable material and contains therein an antimicrobiotic agent, the solubility of the antimicrobiotic agent being chosen in such a way that it is delivered substantially throughout the entire degradation time of the material.

25 Claims, 6 Drawing Sheets

■ 20 cycles Poly (D.L-lactid-co-glycolid) 75/25
◆ 40 cycles Poly (D.L-lactid-co-glycolid) 75/25
▲ 60 cycles Poly (D.L-lactid-co-glycolid) 75/25

IMPLANT, ITS USE IN SURGERY AND PROCESSES FOR THE PRODUCTION THEREOF

TECHNICAL FIELD

The present invention relates to an implant, its use in surgery and processes for the production thereof.

BACKGROUND OF THE INVENTION

Infections after surgery, particularly in vascular or artery surgery, constitute an acute risk for the life of the patient and frequently lead to the amputation of the treated extremity. The problem of prosthesis infection is discussed in detail in medical literature.

In the systemic administration of antibiotics for bringing about infection protection, difficulties occur in setting an optimum serum level, risks such as resistance formation and side-effects prejudicial to the patient. Therefore implants have been developed, which are provided with antimicrobial active agents such as e.g. bactericidal heavy metals or antibiotics.

More recent developments cover the modification of artery or vascular prosthesis material with antibiotics for prophylaxis against infection.

U.S. Pat. No. 4,442,133 describes a process for producing a vascular prosthesis on whose surface is bound an antibiotic. The surface of the prosthesis, of PTFE or polyethylene terephthalate, is firstly treated with an aqueous solution of tridodecyl methyl ammonium chloride (TDMA) or benzalkonium chloride. Following said activation of the prosthesis surface with the positively charged anchor molecule, in the second process step an anionic antibiotic such as penicillin or oxicillin is bound to the prosthesis surface by means of the anchor group by again immersing the prosthesis.

The risk that with the antibiotic unneutralized, surface-active anchor groups act in a blood-damaging and thrombogenic manner, is eliminated in U.S. Pat. No. 4,740,382 in that free, unoccupied anchor molecules are removed from the prosthesis surface again with a cation exchanger sepharose-cm or sulphopropyl cellulose.

The disadvantage that with the hitherto described processes only negatively charged antibiotics can be bound to the prosthesis surface is eliminated by U.S. Pat. No. 4,749,585 in that by means of negatively charged, surface-active anchor molecules, such as e.g. alkyl acrylic sulphonates cationic antibiotics can occupy the prosthesis surface. The further disadvantage that only charge-carrying antibiotics can be used in the process and it is not possible to control the antibiotic delivery rate, is eliminated in that to the cationically activated prosthesis surface are bound negatively charged phospholipid vesicles (liposomes), containing the antibiotic in encapsulated form. The process can also be used with a negatively charged surface and a positively charged liposome.

Further processes for producing more infection-resistant implants are described by Fox and Modark in U.S. Pat. Nos. 4,563,485, 4,581,028, 4,612,337 and EP 207624. These processes are based on the multiple impregnation of the implants with antibiotic-containing solutions of quinolines or sulphonamides and binding the antibiotic in the form of the silver salt to the implant surface.

EP 328421 describes the production of more infection-resistant implant surfaces by using a matrix-forming, polymeric material and a silver salt of a bioguanide (specifically chlorohexidine), in that the polymer and antimicrobial agent are mixed together to form a coating composition with which the implant surface can then be coated.

Antibiotic collagen formulations for coating porous carriers with the aim of permitting a continuous release of active substance from the implant after implantation are also described in DE 3503126.

The described processes have important disadvantages. Thus, in part they are technically very complicated, as well as time and labour-intensive, because several steps must be performed a number of times. In part, a direct preparation in the operating theatre is necessary. Undesired effects such as toxic reactions and increased thrombogenicity are possible. In addition, as a result of subsequent treatment steps, such as the crosslinking of an antibiotic-containing collagen coating, there can be undesired secondary reactions of the crosslinking agent with the antibiotic.

The problem therefore arises of making available an implant with antimicrobiotic action, which can be safely and reliably used to the advantage of the patient and which can be inexpensively manufactured using simple procedures.

SUMMARY OF THE INVENTION

This problem is solved by an implant, which at least partly and at least on the infection-protected surface areas is made from resorbable material and contains therein an antimicrobiotic agent, which is characterized in that the solubility of the antimicrobiotic agent is chosen in such a way that it is delivered essentially throughout the degradation time of the resorbable material.

The implant according to the invention can in particular be constructed in such a way that the solubility of the antimicrobiotic agent and the degradation time of the resorbable material are so matched to one another that the antimicrobiotic agent is delivered in decreasing quantities throughout the degradation time of the material. Advantageously the release kinetics of the antimicrobiotic agent are characterized by a controlled release effect during active substance delivery. The active substance is released according to a diffusion mechanism. In this way the main quantity of the antimicrobiotic agent can be supplied during the first days after surgery, where the infection risk is greatest. In the initial phase the active substance delivery can take place in substantially continuously decreasing quantities. Through the simultaneous degradation of the resorbable material containing the antimicrobiotic agent, the diffusion path to be covered by it decreases, which counteracts a reduced active substance delivery as a result of concentration reduction in the resorbable material.

The implant according to the invention is advantageously constructed in such a way that it has a non-resorbable base, which has at least one coating or impregnation containing the antimicrobiotic agent. Examples for such implants according to the invention are plates, nails, screws, hip joints, catheters or similar medical equipment.

DETAILED DESCRIPTION OF THE INVENTION

In particular the implant can be in the form of a textile fabric, particularly for vascular surgery. According to a preferred embodiment the implant is in the form of an artery or vascular prosthesis. The implant according to the invention can, in a particularly preferred embodiment, be a prefabricated vascular prosthesis. Vascular prostheses are known made e.g. from biological material such as bovine grafts, umbilical cord veins or autologous vein transplants.

Vascular prostheses of synthetic polymers are also conventionally used comprising body-non-resorbable polymers, resorbable polymers or combinations thereof. Examples of non-resorbable implant materials are polytetrafluoroetylene (PTFE), polyesters such as polyethylene terephthalate, polypropylene or polyurethanes, examples for resorbable implant materials are polylactides, polyglycolides, copolymers thereof, glycolidtrimethylene carbonate copolymers, copolymers with other resorbable, cyclic esters or dioxanones, as well as terpolymers thereof.

Implant materials for vascular surgery can be in the form of textile and non-textile fabrics, which are either formed in conventional manner by knitting or weaving and are constructed optionally as velour material, or are produced by spraying, immersing, etc. Such materials can be used as so-called patches for closing or sealing larger openings in vessels or body tissue. In addition, from such textile fabrics can be constructed tubular vascular prostheses. In additional vascular prostheses can be directly formed by producing a tubular structure of implant material, particularly by knitting. Optionally such vascular prostheses can be branched. A particularly preferred embodiment of known vascular prostheses produced from polyester is commercially available under the trademark UNI-GRAFT from B. Braun Melsungen.

In the case of the implant according to the invention a coating of at least one antimicrobiotic agent and at least one resorbable polymer can be formed. Coating can take place according to conventional coating processes known to the expert, such as e.g. dipping or spraying processes. For this purpose the active substance and the resorbable polymer can be applied in an appropriate composition, e.g. in the form of a solution or suspension. Advantageously the antimicrobiotic agent and polymer for the coating are dissolved in the same solvent. Examples of suitable solvents are chloroform, hexafluoroacetone and hexafluoroisopropanol.

According to the invention, it is preferable for the antimicrobiotic agent to be difficultly soluble in water. Advantageously the antimicrobiotic agent has a solubility in water of less than 100 mg/ml, particularly less than 10 mg/ml and preferably less than 1 mg/ml. As a result of the limited solubility of the active substance in water, there is also a delay dissolving of the active substance in vivo. Therefore the active substance is slowly released into the organism over a long period of time with relatively limited concentrations, so that there is a controlled release effect of the active substance. The release behaviour of antimicrobiotic active substances is described in greater detail hereinafter in the examples.

In the implant according to the invention the antimicrobiotic agent can be chosen from the group of substances active against bacteria, fungi and viruses, or a mixture thereof. Antimicrobiotic agents to be used according to the invention are in particular directed against pathological germs for humans, e.g. against gram-positive germs such as *Staphylococcus aureus, Staphylococcus albus* and Streptococcus, gram-negative germs such as *Escherichia coli, Bacterium proteus*, Pseudomonas, Enterococcus and Klebsiella. In an embodiment the antimicrobiotic agent can be an antibiotic. For prophylaxis and therapy with antibiotics use is made in the field of vascular surgery of e.g. cephalosporins such as cephazolin or cephamandol, netilmicin, penicillin such as oxacillin or mezlocillin, tetracycline, metronidazole or aminoglycosides, such as gentamicin or neomycin, as well e.g. rifampin.

In a preferred embodiment the antimicrobiotic agent can be a gentamicin derivative, particularly gentamicin crobefate. Gentamicin crobefate is e.g. commercially available from Merck. According to the invention, the implant is characterized in that the antimicrobiotic agent is present in a concentration of 0.1 to 100 mg, particularly 1 to 10 mg/g of resorbable implant material.

In the implant according to the invention the coating with antimicrobiotic agent and resorbable polymer can be present in a thickness of 0.001 to 1 mm, particularly 0.01 to 0.5 mm. Advantageously the implant according to the invention is characterized in that its entire surface is coated.

According to the invention the release of the antimicrobiotic agent is controlled, but is relatively faster than the decomposition of the resorbable material. The active agent present in controlled release form can be delivered from the resorbable, synthetic polymer film in controlled form over a period of more than 3 days into the implant environment or can be detected on the implant for longer than said period. In particular, the time for the release of the main quantity of the antimicrobiotic agent can be 3 to 15 days, preferably 5 to 15 days. In special embodiments the controlled release of the active agent can last over 20 and up to 100 days. The attainable controlled release effect of the active agent is also linked with the resorbability and therefore the residence time up to the complete resorption of the polymer in vivo. In general, at the end of active substance delivery the polymer is still not completely resorbed. Preferably the released, antimicrobiotic agent quantity is in vivo daily 10 to 500 μg/g of implant material.

The implant according to the invention is advantageously characterized in that the resorbable polymer is a lactide-glycolide polymer. Examples for such resorbable copolymers are formed by poly(D,L-lactide-co-glycolide) with a lactide:glycolide ratio of 75:25 (available under the trademark RESOMER RG 755 from Boehringer Ingelheim) or 50:50 (available under the trademark RESOMER RG 506 from Boehringer Ingelheim). Preferably the resorption time of the polymer in vivo is 1 to 52 weeks, particularly 1 to 12 weeks. Advantageously the polymer is present in a concentration of 500 to 5 mg, particularly 200 to 50 mg/g of implant material. In particular, the implant according to the invention can be characterized in that it entirely comprises resorbable material.

The implant according to the invention can be used in vascular surgery for preventing post-operative infections. Advantageously the use of the implant is characterized by a controlled release of the antimicrobiotic agent.

A process for the production of an implant is characterized in that at least part of the implant is formed by a resorbable material, which contains an antimicrobiotic agent which is difficultly soluble in water and whose release from the resorbable material is of the order of magnitude of the decomposition rate of the resorbable material. In the process according to the invention the release of the antimicrobiotic agent can take place by dissolving as a result of diffusion and/or release as a result of decomposition of the resorbable material. In an embodiment the implant can be made entirely of polymer containing the antimicrobiotic agent. In another embodiment of the process according to the invention a prefabricated implant can be coated with a mixture of at least one antimicrobiotic agent and at least one resorbable polymer.

In a particularly preferred embodiment of the process for producing an implant according to the invention a prefabricated vascular prosthesis can be coated.

Advantageously the process according to the invention is characterized in that coating takes place by spraying, particularly by repeated spraying of a composition of an antimicrobiotic agent and resorbable polymer. In particular, a coating composition can be applied, which contains the antimicrobiotic agent in a concentration of 0.1 to 2 wt. %, based on the total composition and in particular 0.1 to 1 wt. %, and resorbable polymer in a concentration of 0.1 to 5 wt. %, based on the total composition and in particular 0.5 to 1 wt. %.

BRIEF DESCRIPTION OF THE DRAWINGS

Hereinafter the invention is described relative to examples, comparison examples and preferred embodiments, without these having to be looked upon as a restriction. Reference is made to the following drawings, wherein show.

Features of the invention described in the description and claims can be implemented individually or in combination. Known amendments and modifications for desired applications can be made by the expert without leaving the scope of the claimed invention.

EXAMPLES

Comparison Example 1

Coating of resorbable polymer with gentamicin sulphate. A prefabricated vascular prosthesis, commercially available under the trademark UNI-GRAFT, is coated by a spraying process with a suspension of 0.1% gentamicin sulphate and 0.5% of a lactide-glycolide copolymer in chloroform. In the thus prepared vascular prosthesis the readily water-soluble, antimicrobiotic agent is present in the additional coating layer of resorbable polymer. The release kinetics of the active substance is determined by inserting prosthesis portions of a clearly defined length at 37° C. in phosphate buffer and changing the buffer solution after 1, 3, 5, 7 and 24 h. The determination of the gentamicin sulphate content in the buffer solution is performed microbiologically in an agar diffusion test with *S. aureus*. The results given in the following table show that no advantageous controlled release effect can be obtained by introducing a water-soluble active substance into a resorbable polymer layer.

| Spraying cycles | Release gentamicin quantity (mg/g prosthesis) | | | | |
|---|---|---|---|---|---|
| | 1 h | 3 h | 5 h | 7 h | 24 h |
| 20 | 1.7 | 0.1 | n.d. | n.d. | n.d. |
| 40 | 2.8 | 0.8 | 0.2 | n.d. | n.d. | n.d. = not detectable

Comparison Example 2

Sealing an active substance coating with a resorbable polymer coating. A prefabricated vascular prosthesis (UNI-GRAFT) is coated in a spraying process with a 0.1% aqueous gentamicin sulphate solution. The active substance coating is sealed with a polymer coating after drying by spraying over with a 0.5% lactide-glycolide copolymer solution in chloroform. The active substance release kinetics are determined as in example 1, the results being given in the following table. Here again no advantageous control release effect can be obtained when using a water-soluble active substance.

| Spraying cycles | Release gentamicin quantity (mg/g prosthesis) | | | | |
|---|---|---|---|---|---|
| | 1 h | 3 h | 5 h | 7 h | 24 h |
| 10 | 0.7 | 0.1 | n.d. | n.d. | n.d. |
| 20 | 0.9 | 0.2 | n.d. | n.d. | n.n. | n.d. = not detectable

The following examples relate to the controlled release of active substance from a coating of resorbable, hydrolyrically decomposable polymer.

Example 3

The following solutions are prepared for producing implants with a coating of a resorbable, hydrolyticall decomposable polymer containing the difficultly soluble gentamicin salt gentamicin crobefate:

1% poly(D,L-lactide-co-glycolide) 75:25 (commercially available as RESOMER RG 755 from Boehringer Ingelheim) and 0.71% gentamicin crobefate in chloroform, 1% poly-L-lactide (commercially available as RESOMER L 210 from Boehringer Ingelheim) and 0.32% gentamicin crobefate in chloroform.

The solutions are applied by spraying methods with 40 spraying cycles to prefabricated vascular prosthesis (UNI-GRAFT), so that a polymer/active substance layer is formed. The active substance release kinetics are determined by inserting prosthesis portions of defined length and weight in in each case 5 ml of phosphate buffer at 37° C. The leaching medium is replaced every 24 hours during the test period lasting 7 days. The gentamicin base content in the buffer solution is determined microbiologically in the Hemmhof test using *B. subtllis* ATGG 6633 in the detection medium antibiotic agar No. 5 (commercially available from Merck) according to DIN 58940. The reference is gentamicin with 40 mg/ml of biologically active gentamicin (manufacturer Merck). The test results are given in the following table and shown graphically in FIG. 1.

Figure 1:
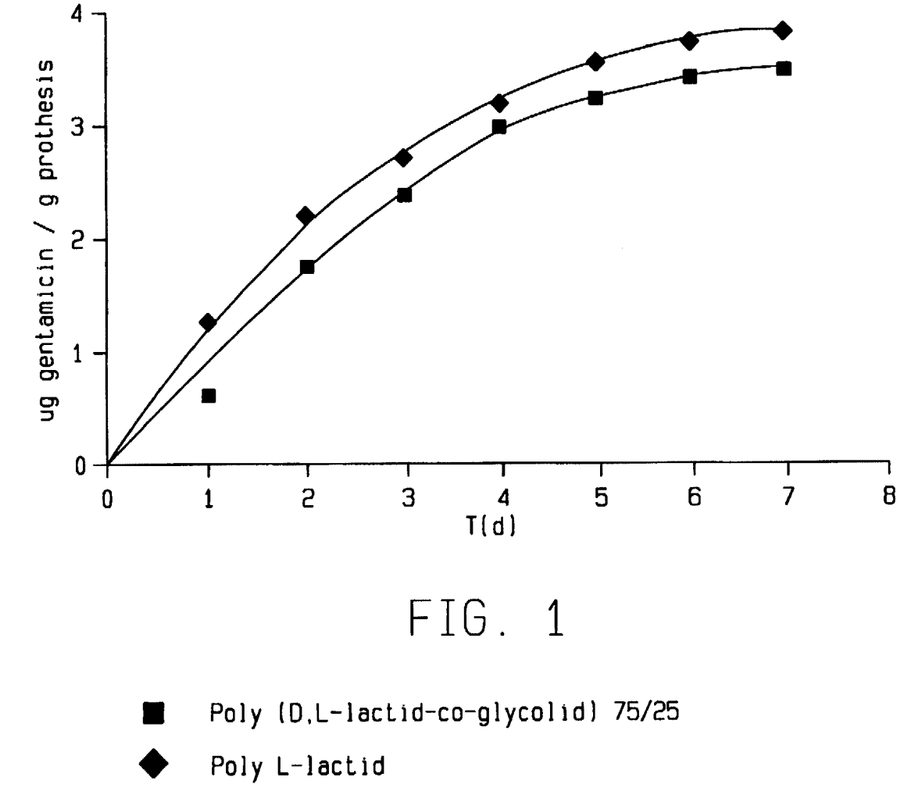
FIG. 1 The in vitro release of gentamicin crobefate from coatings with poly(D,L-lactide-co-glycolide) 75:25 and poly-L-lactide.

It is shown that through the combined use of a difficultly soluble active substance and a resorbable polymer a controlled release of the antimicrobiotic active substance is obtained.

Following the test period of 7 days a cutoff prosthesis ring was placed on antibiotic agar inoculated with *B. subtilis*. A clear Hemmhof was revealed for both active substance formulations, which shows that even after 7 days active quantities of active gentamicin base are still contained in the polymer layer.

|  | Released gentamicin base quantity (mg gentamicin base/g prosthesis) | | | | | | |
|---|---|---|---|---|---|---|---|
| Polymer | 1 d | 2 d | 3 d | 4 d | 5 d | 6 d | 7 d |
| RESOMER RG 755 | 0.61 | 1.14 | 0.61 | 0.61 | 0.27 | 0.18 | 0.08 |
| RESOMER L 210 | 1.26 | 0.93 | 0.50 | 0.50 | 0.37 | 0.18 | 0.08 |

Example 4

For producing implants with a coating of a resorbable, hydrolyrically decomposable polymer containing the difficultly soluble gentamicin salt gentamicin crobefate, a chloroform solution is preferred containing 0.38% gentamicin crobefate and 1% poly(D,L-lactide-co-glycolide) 75:25. This solution is sprayed with an additional antimicrobiotic agent-containing coating at a spraying pressure of 3.5 bar using a spray gun with a nozzle diameter of 0.3 mm for producing prefabricated vascular prostheses (UNI-GRAFT). By varying the spraying cycles performed prostheses are obtained with polymer films of different thicknesses. Thus, as a function of the number of spraying cycles, the active substance content of the polymer film and therefore the prosthesis is varied.

The active substance release kinetics from the thus produced implants are determined by inserting test portions of defined length and weight in in each case 5 ml of phosphate buffer (pH 7.4) at 37° C. The leaching liquid is replaced every 24 hours by fresh phosphate buffer over a test period of 10 days. The gentamicin base concentration determination in the leaching liquid is carried out microbiologically according to DIN 58 940 in the Hemmhof test using *S. aureus*. The results are given in the following table and in FIG. 2.

Figure 2:
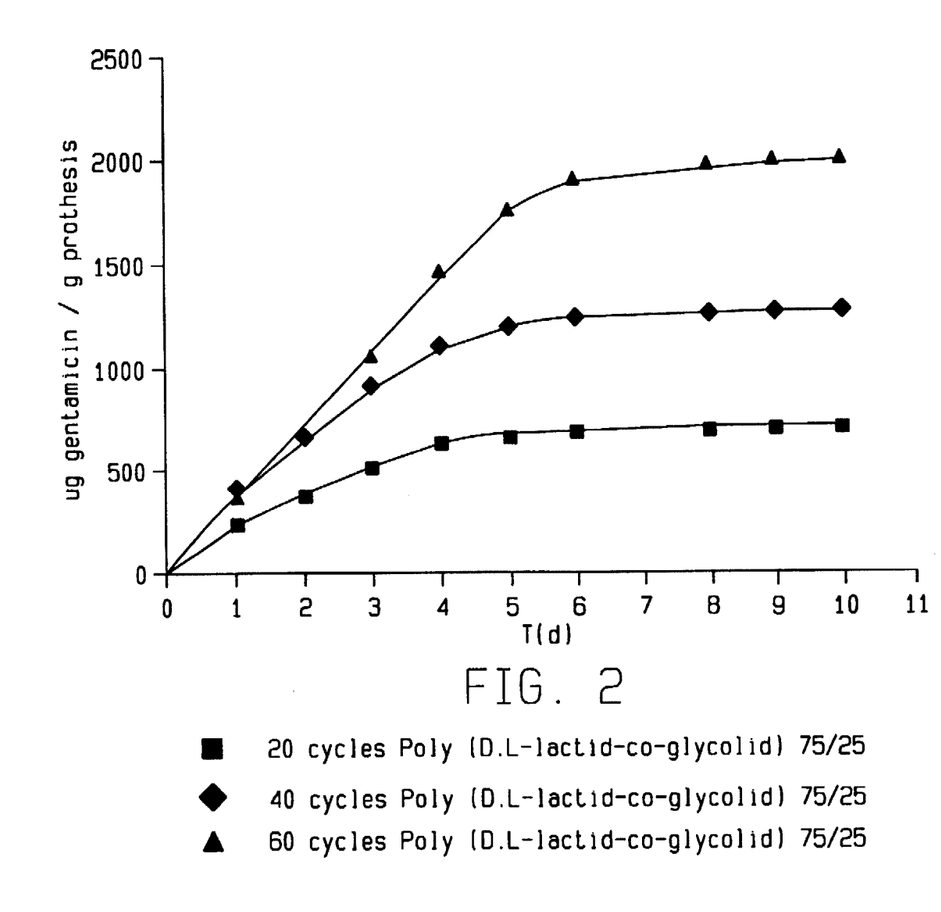
FIG. 2 The cumulative in vitro release of gentamicin crobefate from coatings with poly(D,L-lactide-co-glycolide) 75:25 as a function of the active substance content in the coating.

|  | Release of gentamicin base (µg gentamicin base/g prosthesis) | | | | | | | | | |
|---|---|---|---|---|---|---|---|---|---|---|
| Cycles | 1 d | 2 d | 3 d | 4 d | 5 d | 6 d | 7 d | 8 d | 9 d | 10 d |
| 20 | 231 | 135 | 135 | 118 | 35 | 27 | — | 13 | 6 | 5 |
| 40 | 414 | 245 | 245 | 195 | 99 | 48 | — | 18 | 11 | 8 |
| 60 | 368 | 299 | 384 | 406 | 294 | 159 | — | 72 | 15 | 13 |

Example 5

Prefabricated vascular prostheses are treated according to example 4 with 0.3% gentamicin crobefate and 1% poly(D,L-lactide-co-glycolide) 50:50 in chloroform under a 3.5 bar spraying pressure and with a nozzle diameter of 0.3 mm. The release kinetics were determined according to example 4. The results are given in the following table and in FIG. 3.

Figure 3:
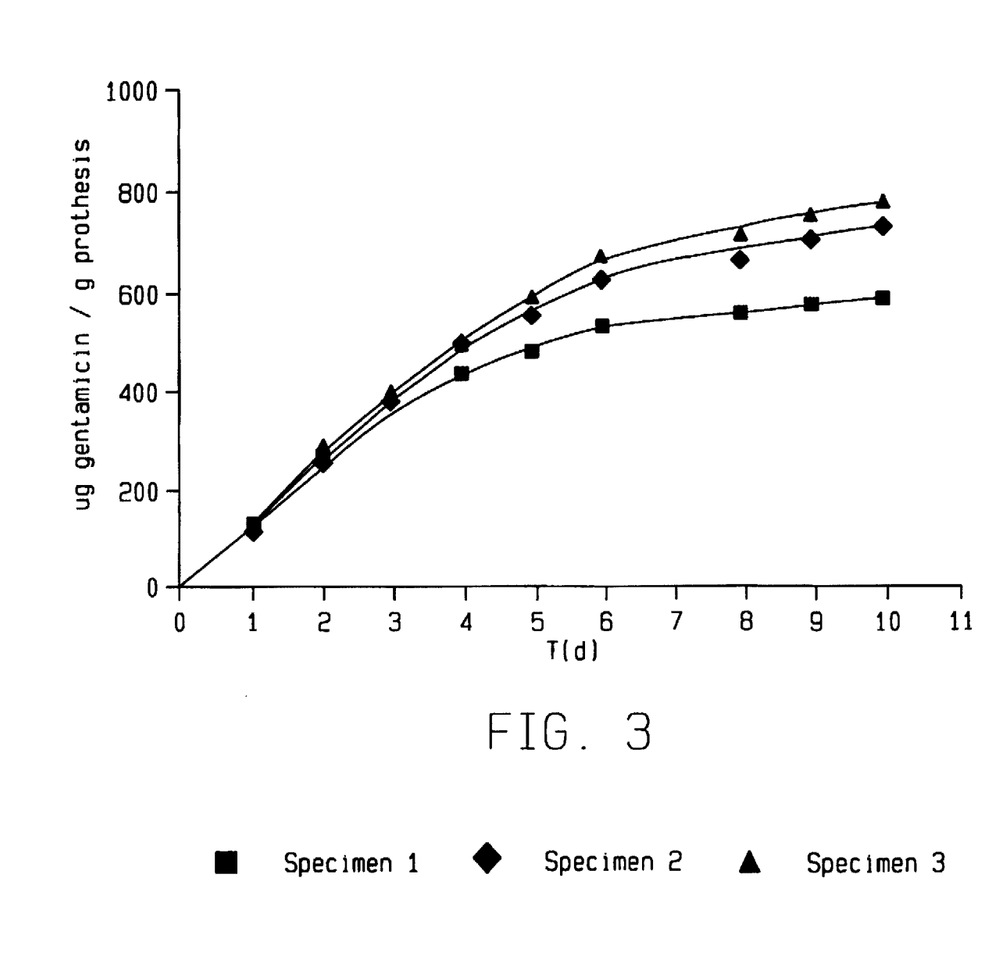
FIG. 3 The cumulative in vitro release of gentamicin crobefate from coatings with poly(D,L-lactide-co-glycolide) 50:50 as a function of the active substance content in the coating.

| Specimen | Gentamicin base release (µg/gentamicin base/g prosthesis) | | | | | | | | | |
|---|---|---|---|---|---|---|---|---|---|---|
| 1 | Cycles | 1 d | 2 d | 3 d | 4 d | 5 d | 6 d | 7 d | 8 d | 9 d | 10 d |
| 1 | 20 | 127 | 143 | 106 | 52 | 45 | 50 | — | 27 | 17 | 11 |
| 2 | 40 | 107 | 141 | 138 | 107 | 54 | 73 | — | 39 | 39 | 16 |
| 3 | 60 | 128 | 162 | 107 | 90 | 96 | 86 | — | 41 | 37 | 26 |

A determination of the residual gentamicin base content on the prosthesis at the end of the release experiment gives the following overall balance:

| Specimen | gentamicin base released (mg/g prosthesis) | gentamicin base residual content (mg/g prosthesis) | gentamicin base total quantity (mg/g prosthesis) |
|---|---|---|---|
| 1 | 0.58 | 0.54 | 1.12 |
| 2 | 0.73 | 1.08 | 1.81 |
| 3 | 0.77 | 2.38 | 3.13 |

Example 6

In vitro release. Prefabricated vascular prostheses are produced in accordance with example 4 under the following conditions: 0.3% gentamicin crobefate, 1% poly(D,L-lactide-co-glycolide) 50:50, 3.5 bar spraying pressure, 0.5 mm nozzle diameter and 60 spraying cycles.

The in vitro determination of the release kinetics takes place in accordance with example 4. The results are given in the following table and in FIG. 4.

Figure 4:
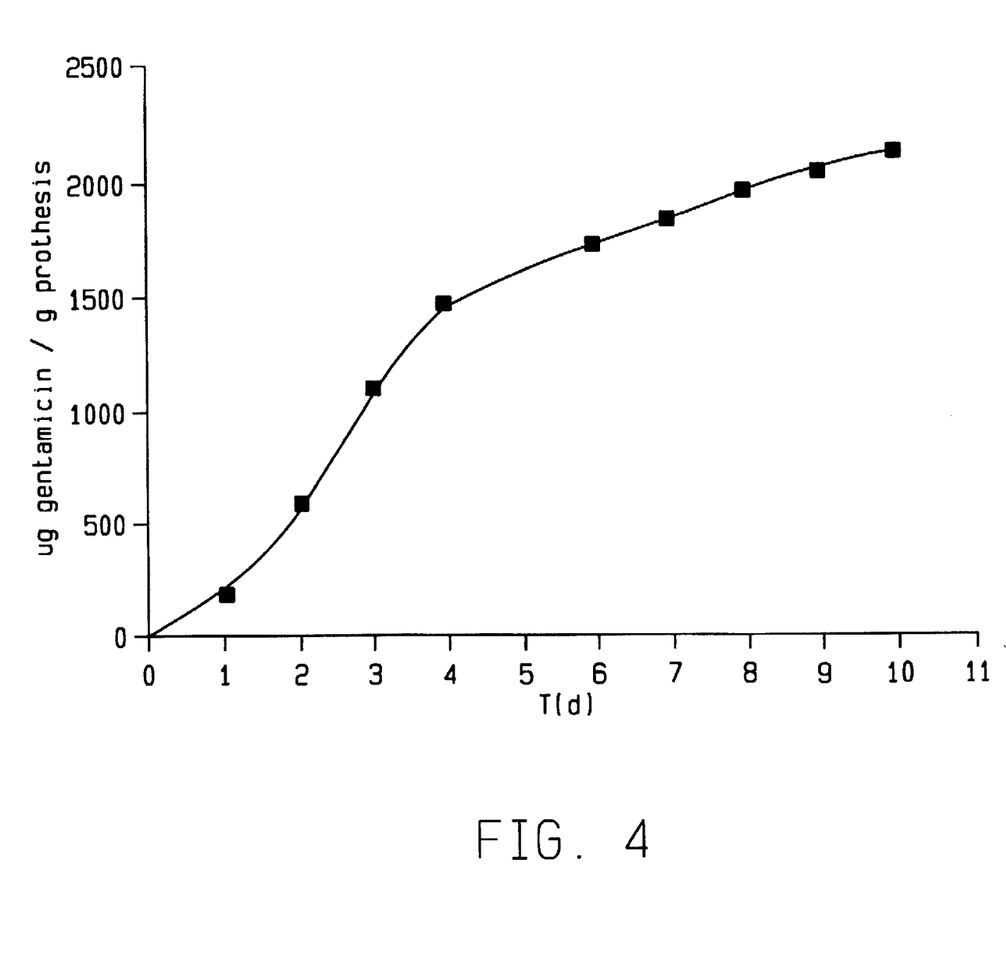
FIG. 4 The cumulative in vitro release of gentamicin crobefate from coatings with poly(D-L-lactide-co-glycolide) 50:50 of an embodiment of the invention.

| Gentamicin base release (µg gentamicin base/g prosthesis) cumulative | | | | | | | | |
|---|---|---|---|---|---|---|---|---|
| 1 d | 2 d | 3 d | 4 d | 6 d | 7 d | 8 d | 9 d | 10 d |
| 181.0 | 409.8 | 501.6 | 375.7 | 251.7 | 119.3 | 119.3 | 83.4 | 83.4 |

At the end of the in vitro release test in each case one prosthesis ring is placed on antibiotic agar inoculated with *S. aureus*. There is an inhibition of on average 31 mm (determination limit 10 mm). This shows that even after 10 days in the release test, significant quantities of active gentamicin base are still contained in the polymer layer.

The determination of the total active substance content on the prosthesis (3.5 mg gentamicin base/g prosthesis) reveals an active substance release of in all approximately 60% after 10 days.

In vivo release. For investigating the release kinetics of gentamicin from the implants in vivo, active substance-containing vascular prostheses were functionally implanted in the dog by infrarenal aortic replacement. The antibiotic level was determined in the serum, urine and wound exudations. The test period lasted 72 hours.

The antibiotic concentration in the serum was determined microbiologically in the agar diffusion test. The determination limit was 0.06 µg/ml (calibration curve gentamicin sulphate in serum). The antibiotic could at no point be detected in the serum.

Figure 5:
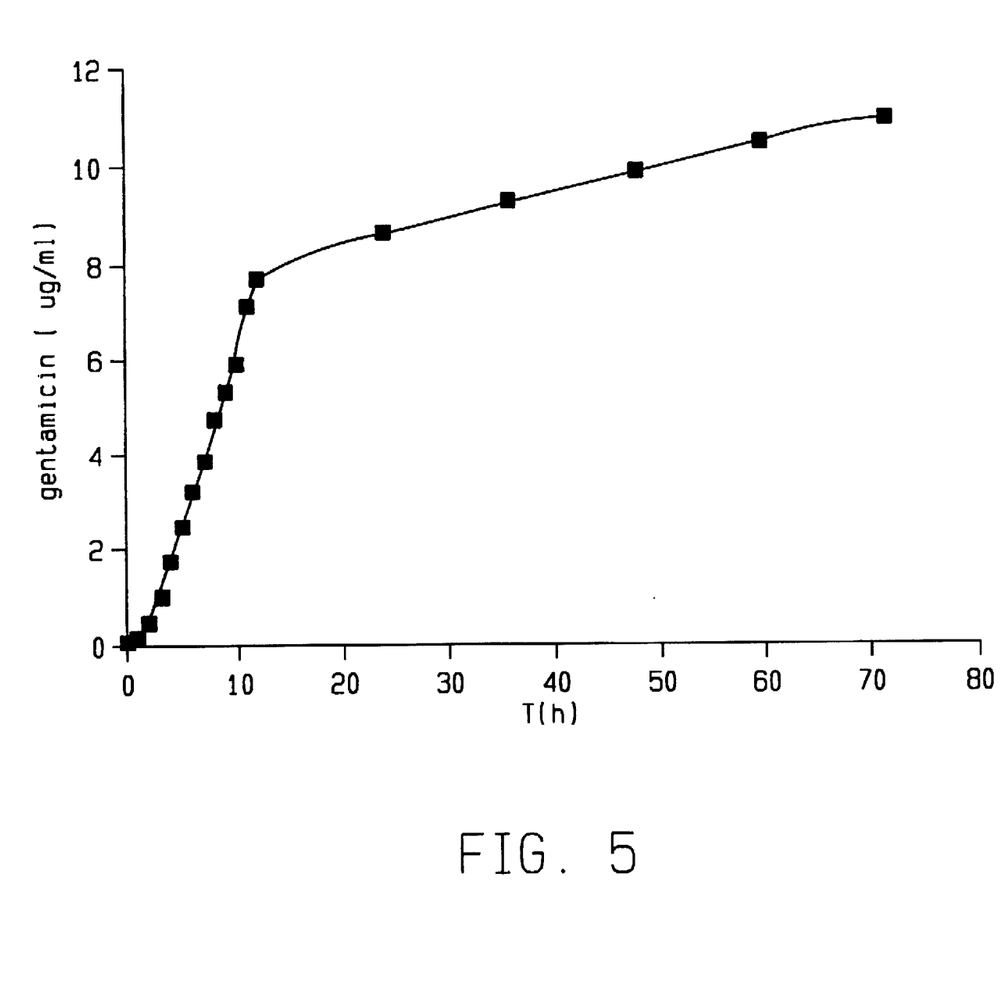
FIG. 5 The microbiological determination of the in vivo release of gentamicin crobefate in the urine (dog).

The antibiotic concentration in the urine was determined microbiologically in the agar diffusion test. The determination limit was 0.06 µg/ml (calibration curve gentamicin sulphate in the urine). The results are summarized in the following table 1 and shown graphically in FIG. 5. Gentamicin was detected in the urine throughout the test period.

Figure 6:
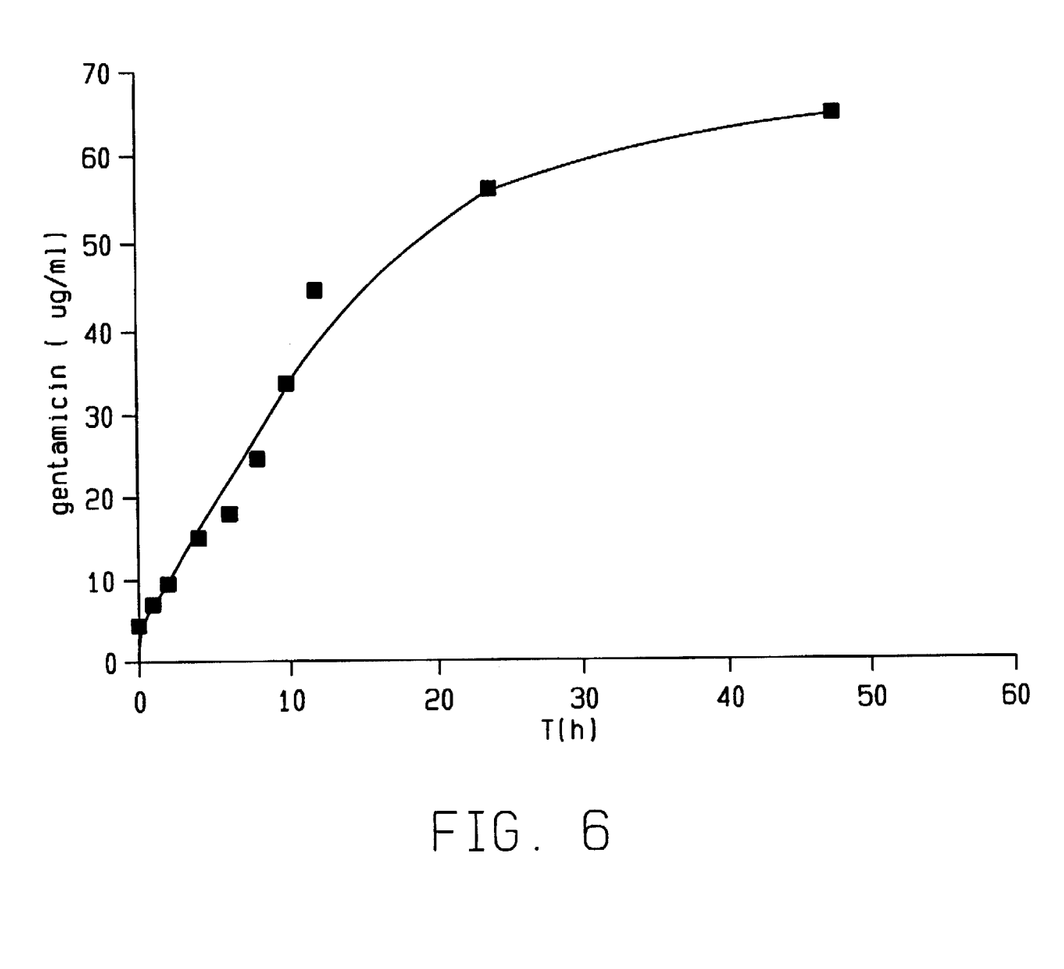
FIG. 6 The microbiological determination of the in vivo release of gentamicin crobefate in wound exudation (dog).

The antibiotic concentration in the wound exudations took place microbiologically in the agar diffusion test. The determination limit was 0.06 µg/ml (calibration curve gentamicin sulphate in serum). The results are summarized in table 1 and graphically shown in FIG. 6. Due to lack of wound exudation, a determination was only possible over a 48 hour period. Gentamicin was detected in the wound exudation over the entire test period.

At the end of the test the prosthesis was explanted. Prosthesis rings were placed on antibiotic agar inoculated with *s. aureus* and the Hemmhof was measured.

| Explantation after | 12 h | 24 h | 48 h | 72 h |
|---|---|---|---|---|
| Hemmhof diameter | 31 mm | 30 mm | 28 mm | 24 mm |

Even after 72 h implantation a definite active gentamicin base quantity was still determined on the implant.

TABLE 1

| Microbiological determine of gentamicin release, cumulative. | | |
|---|---|---|
| Time (h) | Urine (µg/ml) | Wound exudation (µg/ml) |
| p. op. | 0.07 | 4.50 |
| 1 | 0.19 | 7.07 |
| 2 | 0.48 | 9.58 |
| 3 | 1.01 | — |
| 4 | 1.75 | 15.06 |
| 5 | 2.49 | — |
| 6 | 3.23 | 18.03 |
| 7 | 3.86 | — |
| 8 | 4.75 | 24.54 |
| 9 | 5.30 | — |
| 10 | 5.92 | 33.66 |
| 11 | 7.16 | — |
| 12 | 7.72 | 44.55 |
| 24 | 8.60 | 55.67 |
| 36 | 9.23 | — |
| 48 | 9.86 | 64.79 |
| 60 | 10.46 | — |
| 72 | 10.89 | — |

I claim:

1. An implant, having infection-protected surface areas, which at least partly and at least on the infection-protected surface areas comprises resorbable material having a degradation time, the resorbable material containing an antimicrobiotic agent, wherein the solubility of the antimicrobiotic agent is chosen in such a way that the antimicrobiotic agent is delivered substantially over the entire degradation time of the resorbable material, and wherein the solubility of the antimicrobiotic agent and the degradation time of the resorbable material are matched to one another, so that the antimicrobiotic agent is delivered in decreasing quantities during the degradation time.

2. The implant according to claim 1, wherein the implant has a non-resorbable base, which has at least one coating or impregnation containing the antimicrobiotic agent.

3. The implant according to claim 2, wherein the coating is formed from at least one antimicrobiotic agent and at least one resorbable polymer.

4. The implant according to claim 3, wherein the antimicrobiotic agent is slightly soluble in water.

5. The implant according to claim 3, wherein the antimicrobiotic agent has a solubility in water of less than 100 mg/ml.

6. The implant according to claim 3, wherein the antimicrobiotic agent is at least one agent of the group consisting of substances active against bacteria, fungi and viruses and mixtures thereof.

7. The implant according to claim 3, wherein the antimicrobiotic agent is an antibiotic.

8. The implant according to claim 3, wherein the antimicrobiotic agent is a slightly soluble gentamicin derivative.

9. The implant according to claim 3, wherein the antimicrobiotic agent is present in a concentration of 0.1 to 100 mg of resorbable implant material.

10. The implant according to claim 3, wherein the coating with antimicrobiotic agent and resorbable polymer is present in a thickness of 0.001 to 1 mm.

11. The implant according to claim 3, wherein the antimicrobiotic agent is released in controlled manner, but more rapidly than the resorbable material is decomposed.

12. Implant according to claim 3, wherein the time for the in vivo release of the main quantity of the antimicrobiotic agent is 3 to 15 days.

13. The implant according to claim 3, wherein a in vivo released antimicrobiotic agent quantity per day is 10 to 500 µg/g of implant material.

14. The implant according to claim 1, wherein the implant is in the form of a textile structure.

15. The implant according to claim 1, wherein the implant is in the form of a vascular prosthesis.

16. The implant according to claim 1, wherein the entire implant surface is coated.

17. The implant according to claim 1, wherein the resorbable material is a lactide-glycolide copolymer.

18. The implant according to claim 1, wherein the in vivo resorption time of the resorbable material is 1 to 52 weeks.

19. Implant according to claim 1, wherein it entirely comprises resorbable material.

20. A process for producing an implant according to claim 1, wherein at least part of the implant is formed from a resorbable material, which contains an antimicrobiotic agent which is slightly soluble in water and whose release from the resorbable material is of the order of magnitude of the decomposition rate of the resorbable material.

21. The process according to claim 20, wherein a prefabricated implant is coated with a mixture of at least one antimicrobiotic agent and at least one resorbable polymer.

22. The process according to claim 20, wherein a prefabricated vascular prosthesis is coated.

23. The process according to claim 20, wherein the coating takes place by at least one spraying of a composition with antimicrobiotic agent and resorbable polymer.

24. The process according to claim 20, wherein a liquid coating composition is applied, which has the antimicrobiotic agent in a concentration of 0.1 to 2 wt %, based on the total composition and resorbable polymer in a concentration of 0.1 to 5 wt. %, based on the total composition.

25. An implant, having infection-protected surface areas, which at least partly and at least on the infection-protected surface areas comprises resorbable material having a degradation time, the resorbable material containing an antimicrobiotic agent that is slightly soluble in water, wherein the solubility of the antimicrobiotic agent and the degradation time of the resorbable material are matched to one another, so that the antimicrobiotic agent is delivered substantially over the entire degradation time of the resorbable material, and the antimicrobiotic agent is delivered in decreasing quantities during the degradation time, and wherein the resorbable material is selected from the group consisting of polylactides, polyglycolides, copolymers thereof, glycolide-trimethylene-carbonate copolymers, and copolymers of resorbable cyclic esters and dioxanones and terpolymers thereof.

* * * * *